Feb. 2, 1960 H. C. SWIM Plant Pat. 1,904
ROSE PLANT
Filed Jan. 8, 1959
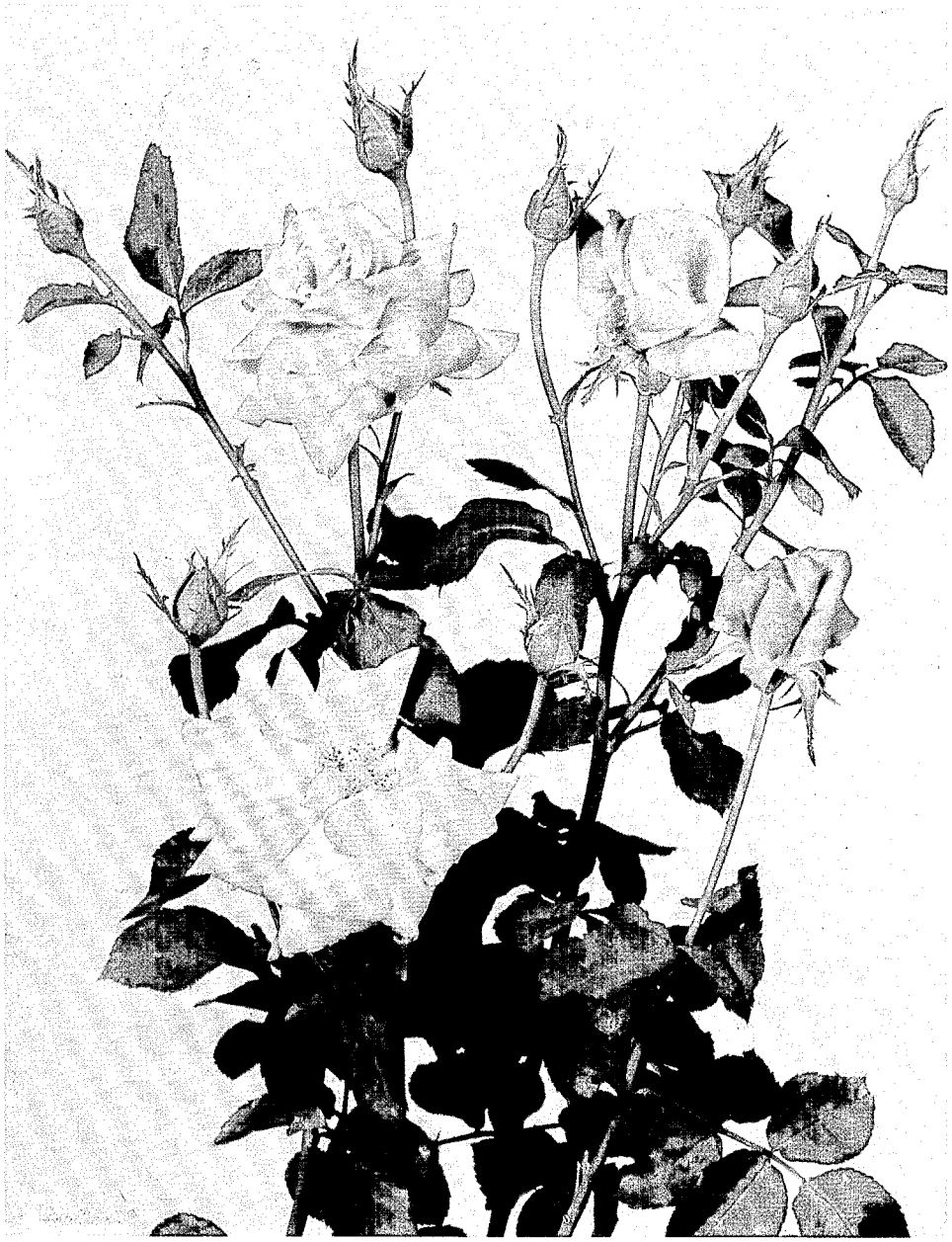
Inventor.
H. C. Swim
By: Robb & Robb
Attorneys.

United States Patent Office

Plant Pat. 1,904
Patented Feb. 2, 1960

1,904

ROSE PLANT

Herbert C. Swim, Ontario, Calif., assignor to Armstrong Nurseries, Inc., Ontario, Calif., a corporation of California Application January 8, 1959, Serial No. 785,770

1 Claim. (Cl. 47—61)

The present invention relates to a new and distinct variety of rose plant of the class falling between the hybrid tea and floribunda classes, which was originated by me by crossing the variety "First Love" (Plant Patent No. 921) with the variety "Pinocchio" (Plant Patent No. 484).

The general objective of this breeding was to produce a new rose variety having a floriferousness approaching that of the pollen parent "Pinocchio," and a bud form approaching that of the seed parent "First Love," combined with a vigorous and disease-resistant plant habit, flower stems of medium length, flowers of double form, and an attractive flower color. This general objective was achieved, along with other desirable improvements, as evidenced by the following unique combination of characteristics which are outstanding in the new variety and which distinguish it from its parents, as well as from all other varieties of which I am aware:

(1) A vigorous, much-branched and bushy plant habit;

(2) Attractive, disease-resistant foliage of medium size;

(3) A fluoriferousness at least midway between that of "First Love" and "Pinocchio," and more probably approaching that of "Pinocchio";

(4) A habit of bearing flowers sometimes singly and sometimes in small clusters, with the flowers usually borne on stems of medium length;

(5) An attractive bud form ranging from ovoid to urn-shaped, said bud opening to a flower of double form, with moderate petalage;

(6) A flower size midway between that of "First Love" and "Pinocchio"; and (7) A general color tonality of the flowers of medium pink, blending in areas to a lighter pink color.

In comparison with its seed parent, "First Love," the new variety is more bushy and more branched; more floriferous and with the flowers borne more in small clusters, as distinguished from the flowers of "First Love" which are usually borne singly and are larger, and the color of the blooms is usually a somewhat darker pink.

As compared with its pollen parent, "Pinocchio," the new variety is more vigorous; it is somewhat less fluoriferous; its flowers are borne on somewhat longer stems; the buds are somewhat longer and more urn-shaped; and the flowers are less double in petalage and somewhat larger.

A sexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious:

Type: Bush; outdoor; seedling; for cut flowers and for garden decoration.

Class: Between hybrid tea and hybrid polyantha.

Breeding: Seedling.

*Seed parent.*—"First Love."

*Pollen parent.*—"Pinocchio."

Propagation: Holds its distinguishing characteristics through succeeding propagations by budding.

*Flower*

Locality where grown and observed: Ontario, California.

Flowers borne: Sometimes singly, but usually from 2 to 5 or more to stem; in irregular clusters; on stems of from normal strength to strong and from short to medium length.

Quantity of bloom: Abundant, outdoors.

Continuity: Nearly continuous during growing season.

Fragrance: Slight.

Bud:

*Peduncle.*—Average length; average caliper; erect; almost smooth; usually with some stipitate glands. Color—near Dull Green Yellow, Plate XVII (Ridgway), overlaid with near Ocher Red, Plate XXVII (Ridgway) on side exposed to the sun.

*Before calyx breaks.*—Size—from small to medium. Form—medium length; ovoid.

*As calyx breaks.*—Color—near Spinel Red, Plate 0023, page 189 (Wilson).

*Sepals.*—Inner surface—with fine, wholly tomentum. Outer surface—moderately smooth; with some stipitate glands. Alternate margins—lined with fine, wholly tomentum. Other margins—lined with stipitate glands and slender foliaceous appendages, with foliaceous parts extending beyond tip equal to ⅓ or more of its length.

*As first petal opens.*—Size—from small to average. Form—ovoid to urn-shaped. Color: outside—between Crimson, Plate 22/1, page 22 (Wilson) and Rose Madder, Plate 23/2, page 23 (Wilson), with small area at base of petal near Mimosa Yellow, Plate 602, page 143 (Wilson); inside—near Rose Madder, Plate 23/1, page 23 (Wilson), with small area at base of petal near Mimosa Yellow, Plate 602, page 143 (Wilson).

*Opening.*—Opens up well; is not retarded from opening by cold, hot, wet or dry weather.

Bloom:

*Size (when fully open).*—Average; from 3½ inches to 4¼ inches.

*Petalage.*—Double; from 20 to 25 petals plus from 0 to 4 petaloids; arranged regularly.

*Form.*—High-centered at first, but becoming from cupped to high-centered; petals being at first somewhat loosely cupped, becoming later more loosely flat to cupped at maturity; lateral margins of inner petals usually reflexed from ½ to ⅔ of petal length, with tip of petal sometimes rolled outward; lateral margins of intermediate and outer petals usually reflexed ⅔ of petal length, with tips of petals usually rolled outward.

Petals:

*Texture.*—Medium thickness. Inside—satiny. Outside—satiny.

*Shape.*—Outer—from near round to broadly obovate, with apex flat. Intermediate—broadly obovate, with apex from rounded to flat. Inner—obovate, with apex rounded.

This description of a newly opened flower was made from a rose grown outdoors in the month of October at Ontario, California:

*Color.*—Outer petal: outside surface—between Tyrian Rose, Plate 24/3, page 24 (Wilson) and Rhodamine Pink, Plate 527/2, page 138 (Wilson), usually blending with near Rhodamine Pink, Plate 527/3, page 138 (Wilson) toward base of petal, with small area at base near Mimosa Yellow, Plate 602/1, page 142 (Wilson); inside surface—between Tyrian Rose, Plate 24/2, page 24 (Wilson) and Rose Bengal, Plate 25/2, page 25 (Wilson), usually blending with near Rhodamine Pink, Plate 527/2, page 138 (Wilson) toward base of petal, with small area at base near Mimosa Yellow, Plate 602/1, page 143 (Wilson). Intermediate petal: outside surface—between Rose Madder, Plate 23/3, page 23 (Wilson) and Tyrian Rose, Plate 24/3, page 24 (Wilson), sometimes blending into near Dawn Pink, Plate 523/2, page 137 (Wilson), with small area at base of petal near Mimosa Yellow, Plate 602/1, page 143 (Wilson); inside surface—between Rose Madder, Plate 23/2, page 23 (Wilson) and Tyrian Rose, Plate 24/2, page 24 (Wilson), with small area at base of petal near Mimosa Yellow, Plate 602/1, page 143 (Wilson). Inner petal: outside surface—between Carmine, Plate 21/3, page 21 (Wilson) and Crimson, Plate 22/3, page 22 Wilson), with small area at base of petal near Mimosa Yellow, Plate 602/1, page 143 (Wilson); inside surface—between Carmine, Plate 21/2, page 21 (Wilson) and Crimson, Plate 22/2, page 22 (Wilson), with small area at base of petal near Mimosa Yellow, Plate 602/1, page 143 (Wilson).

This description was made from a rose that was open for 3 days outdoors in the month of October at Ontario, California:

*Color.*—Outer petal: outside surface—between Tyrian Rose, Plate 24/3, page 24 (Wilson) and Rhodamine Pink, Plate 527/3, page 138 (Wilson), usually blending with between Rhodamine Pink, Plate 527/3, page 138 (Wilson) and White toward base of petal, with small area at base near Mimosa Yellow, Plate 602/2, page 143 (Wilson); inside surface—between Tyrian Rose, Plate 24/2, page 24 (Wilson) and Rose Bengal, Plate 25/3, page 25 (Wilson), with small area at base of petal near Mimosa Yellow, Plate 602/2, page 143 (Wilson). Inner petal: outside surface—near Rhodamine Pink, Plate 527/2, page 138 (Wilson), with small area at base of petal near Mimosa Yellow, Plate 602/2, page 143 (Wilson); inside surface—near Tyrian Rose, Plate 24/2, page 24 (Wilson), usually blending with near Rose Bengal, Plate 25/3, page 25 (Wilson) toward base of petal. (Inside surfaces of outer and intermediate petals of both newly opened and three days open flower usually somewhat darker in color on areas exposed to the sun which are not shaded by other petals.)

*General color effect.*—Newly opened flower—between Rose Madder, Plate 23/2, page 23 (Wilson) and Tyrian Rose, Plate 24/2, page 24 (Wilson). 3-days open—between Tyrian Rose, Plate 24/2, page 24 (Wilson) and Rose Bengal, Plate 25/3, page 25 (Wilson).

*Behavior.*—Drop off cleanly; not particularly affected by cold, hot, wet or dry weather.

*Flower longevity.*—On bush in garden—4 or 5 days in October. Cut roses grown outdoors and kept at living-room temperatures—5 or 6 days in October.

*Reproductive organs*

Stamens: From average number to many; arranged regularly about pistils.

Filaments: Medium length; from 6 mm. to 12 mm. in length; most with anthers. Color—near Lemon Yellow, Plate 4, page 4 (Wilson).

Anthers: From small to medium size; all open approximately at once. Color: upper side—margins near Yellow Ochre, Plate 07/1, page 101 (Wilson), with remainder near Lemon Yellow, Plate 4, page 4 (Wilson); under side—margins near Yellow Ochre, Plate 07/1, page 101 (Wilson), with remainder near Lemon Yellow, Plate 4, page 4 (Wilson).

Pollen: From moderate abundance to abundant. Color—near Indian Yellow, Plate 6/2, page 6 (Wilson).

Pistils: Many; approximately 110 in number.

Styles: Moderately even; from short to average length; from 4 mm. to 10 mm. in length; from thin to average caliper; bunched. Color—upper ⅓ of style near Crimson, Plate 22/2, page 22 (Wilson), with remainder near Dresden Yellow, Plate 64/2, page 64 (Wilson).

Stigma: Color—near Yellow Ochre, Plate 07/2, page 101 (Wilson).

Ovaries: Usually all enclosed in calyx.

Hips: Average length; globular; moderately smooth; walls thick and fleshy. Color (mature)—near Apricot Orange, Plate XIV (Ridgway).

Sepals: Permanent; medium length; usually straight. Color: inside—near Citrine Drab, Plate XL (Ridgway); outside—near Rainette Green, Plate XXXI (Ridgway).

Seeds: From average number to many; from 35 to 40 in number; usually small.

*Plant*

Foliage:

*Leaves.*—Compound of usually 3 to 7 leaflets; from normal abundance to abundant; medium size; somewhat leathery and semi-glossy.

*Leaflets.*—Shape—from oval to obovate, with apex acute. Base—round. Margin—simply serrate.

*Color.*—Mature: upper surface—between Dark Dull Yellow Green, Plate XXXII (Ridgway) and Empire Green, Plate XXXII (Ridgway); under surface—near Light Elm Green, Plate XVII (Ridgway). Young: upper surface—near Rainette Green, Plate XXXI (Ridgway), with edges of leaflets usually near Dark Vinaceous Brown, Plate XXXIX (Ridgway); under surface—near Citrine, Plate IV (Ridgway), overlaid with near Prussian Red, Plate XXVII (Ridgway).

*Rachis (the supporting stem of the compound leaf).*—Average size. Upper side—smooth; with some stipitate glands on edges. Under side—smooth; with stipitate glands and few small prickles.

*Stipules.*—Medium length; medium width; with from short to medium length points turning out at an angle of less than 45°.

*Disease resistance.*—Better-than-average resistance to mildew, as compared with other varieties grown under comparable cultural conditions at Ontario, California.

Growth:

*Habit.*—Bushy; upright and spreading; much-branched.

*Growth.*—Vigorous.

*Canes.*—Medium caliper.

*Main stems.*—Color—between Grass Green, Plate VI (Ridgway) and Light Elm Green, Plate XVII (Ridgway). Large prickles — several; from medium length to long; almost straight; with medium length, moderately narrow base; color—near Pecan Brown, Plate XXVIII (Ridgway). Small prickles—few; color—near Pecan Brown, Plate XXVIII (Ridgway). Hairs—none.

*Branches.*—Color—near Biscay Green, Plate XVII (Ridgway). Large prickles—few; from medium length to long; hooked slightly downward; with medium length, narrow base; color—near Mikado Brown, Plate XXIX (Ridgway). Small prickles—few; color—near Mikado Brown, Plate XXIX (Ridgway). Hairs—none.

*New shoots.*—Color—near Calliste Green, Plate VI (Ridgway), usually overlaid with near Olive Lake, Plate XVI (Ridgway) on side exposed to the sun. Large prickles—from none to very few; medium length; hooked slightly downward; with medium length, narrow base; color—near Deep Corinthian Red, Plate XXVII (Ridgway). Small prickles—from none to few; color—near Deep Corinthian Red, Plate XXVII (Ridgway). Hairs—none.

I claim:

A new and distinct variety of rose plant of the class between the hybrid tea and florbunda classes, substantially as herein shown and described, characterized particularly as to novelty by its unique combination of a vigorous, much-branched and bushy habit of growth, attractive, disease-resistant, medium sized foliage, a floriferousness midway between that of "First Love" (Plant Patent No. 921) and "Pinocchio" (Plant Patent No. 484), and more probably approaching that of "Pinocchio," a habit of bearing flowers sometimes singly and sometimes in small clusters, with the flowers usually borne on stems of medium length, an attractive bud form ranging from ovoid to urn-shaped, said bud opening to a flower of double form, with moderate petalage, a flower size midway between that of "First Love" and Pinocchio," and a general color tonality of the flowers of medium pink, blending in areas to a lighter pink color.

No references cited.